United States Patent
Kim et al.

(10) Patent No.: US 10,238,481 B2
(45) Date of Patent: Mar. 26, 2019

(54) APPARATUS AND METHOD FOR LIFTING OR RESTRAINING A BODY PART

(71) Applicant: SURGICAL INNOVATION ASSOCIATES, INC., Chicago, IL (US)

(72) Inventors: John Y. S. Kim, Lincolnwood, IL (US); Alexei Mlodinow, Chicago, IL (US); Todd Cruikshank, Chicago, IL (US)

(73) Assignee: Surgical Innovation Associates, Inc., Chicago, IL (US)

( * ) Notice: Subject to any disclaimer, the term of this patent is extended or adjusted under 35 U.S.C. 154(b) by 0 days.

(21) Appl. No.: 15/709,754

(22) Filed: Sep. 20, 2017

(65) Prior Publication Data

US 2018/0078355 A1    Mar. 22, 2018

Related U.S. Application Data

(60) Provisional application No. 62/397,297, filed on Sep. 20, 2016.

(51) Int. Cl.
*A61F 2/00* (2006.01)
*A61B 17/06* (2006.01)
(Continued)

(52) U.S. Cl.
CPC ...... *A61F 2/0063* (2013.01); *A61B 17/06166* (2013.01); *A61F 2/0059* (2013.01); *A61B 17/3468* (2013.01); *A61B 2017/00792* (2013.01); *A61B 2017/00796* (2013.01); *A61B 2017/06052* (2013.01); *A61B 2017/06176* (2013.01); *A61F 2/0045* (2013.01);
(Continued)

(58) Field of Classification Search
CPC .......... A61F 2/00; A61F 2/004; A61F 2/0031; A61F 2/0036; A61F 2/0045; A61F 2/0063; A61F 2/0077; A61F 2002/0068; A61F 2002/0072; A61F 2002/0081; A61F 2002/0086; A61B 2017/06176; A61B 2017/06185
See application file for complete search history.

(56) References Cited

U.S. PATENT DOCUMENTS 4,347,847 A * 9/1982 Usher .................. A61F 2/0063
                                                        128/898
6,485,503 B2   11/2002 Jacobs et al.
(Continued)

OTHER PUBLICATIONS

"Expand." Merriam-Webster.com. Merriam-Webster, n.d. Web. Nov. 15, 2018.*
(Continued)

*Primary Examiner* — Carrie R Dorna
(74) *Attorney, Agent, or Firm* — Drinker Biddle & Reath LLP

(57) ABSTRACT

The disclosure is generally directed to assemblies and methods that include (1) strips or cords of material configured to lift, restrain, or hold whole body organs (e.g., of a human patient) or parts of body organs in desired positions via tissue anchors (e.g., barbs, hooks, or cones), (2) an introducer device that facilitates the introduction of such strips or cords into a patient, and (3) the process of inserting such strips or cords of material into a patient (e.g., using an introducer device).

7 Claims, 7 Drawing Sheets

(51) Int. Cl.
*A61B 17/34* (2006.01)
*A61B 17/00* (2006.01)
(52) U.S. Cl.
CPC ................ *A61F 2002/0068* (2013.01); *A61F 2002/0072* (2013.01); *A61F 2220/0016* (2013.01)

(56) References Cited

U.S. PATENT DOCUMENTS

| | | | |
|---|---|---|---|
| 7,172,615 B2 | 2/2007 | Morriss et al. | |
| 7,510,566 B2 | 3/2009 | Jacobs et al. | |
| 7,972,347 B2 | 7/2011 | Garvin et al. | |
| 8,100,940 B2 | 1/2012 | Leung et al. | |
| 8,721,666 B2 | 5/2014 | Schroeder et al. | |
| 8,821,533 B2 | 9/2014 | Newman et al. | |
| 8,858,577 B2 | 10/2014 | Kubiak | |
| 8,894,683 B2 | 11/2014 | Weadock et al. | |
| 8,945,156 B2 | 2/2015 | Kubiak et al. | |
| 8,974,442 B1 | 3/2015 | Boss, Jr. | |
| 9,427,309 B2 | 8/2016 | Kubiak et al. | |
| 9,451,961 B2 | 9/2016 | Kubiak | |
| 2004/0060409 A1* | 4/2004 | Leung | A61B 17/04 83/522.14 |
| 2005/0261737 A1* | 11/2005 | Sakura | A61B 17/0482 606/215 |
| 2005/0277985 A1* | 12/2005 | Wert | A61B 17/06166 606/228 |
| 2005/0283040 A1* | 12/2005 | Greenhalgh | A61F 2/0045 600/30 |
| 2008/0082113 A1* | 4/2008 | Bishop | A61B 17/06166 606/151 |
| 2008/0262542 A1 | 10/2008 | Sulamanidze et al. | |
| 2014/0228971 A1 | 8/2014 | Kim | |
| 2016/0256252 A1 | 9/2016 | Sim | |

OTHER PUBLICATIONS

Covidien, "Parietex ProGrip Self-Fixating Mesh," Value Analysis Committee Product Information Kit, 2010, 20 pages.
PCT Search Report and Written Opinion issued in related application PCT/US2017/052458, dated Nov. 28, 2017, 8 pages.

* cited by examiner

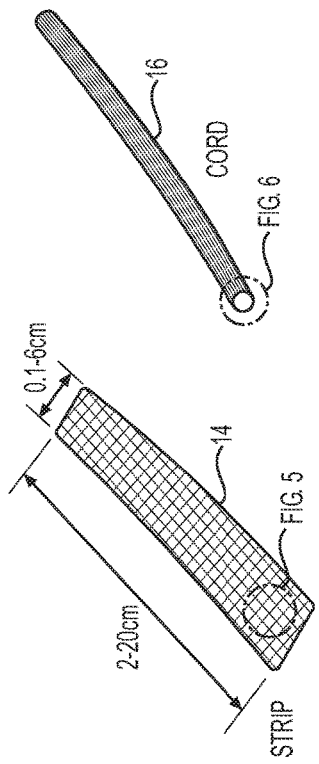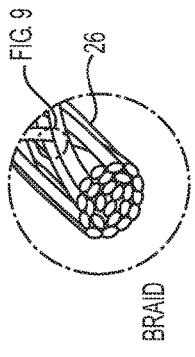
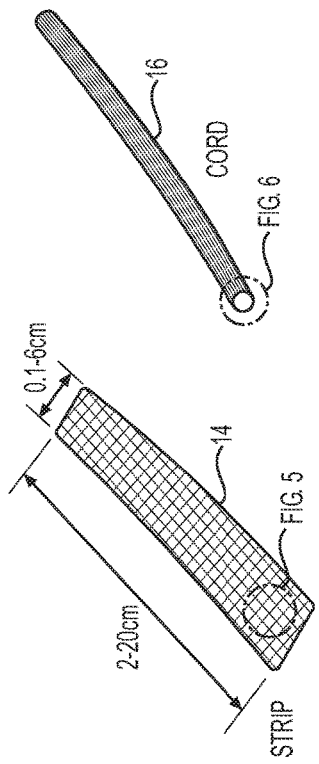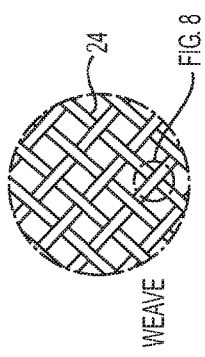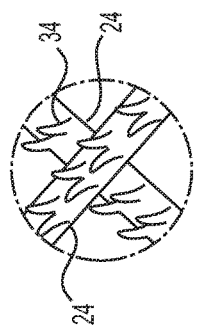
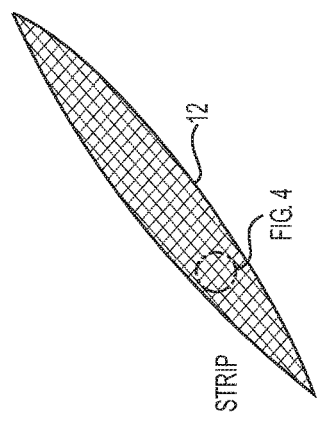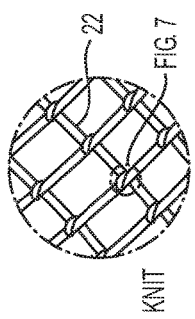

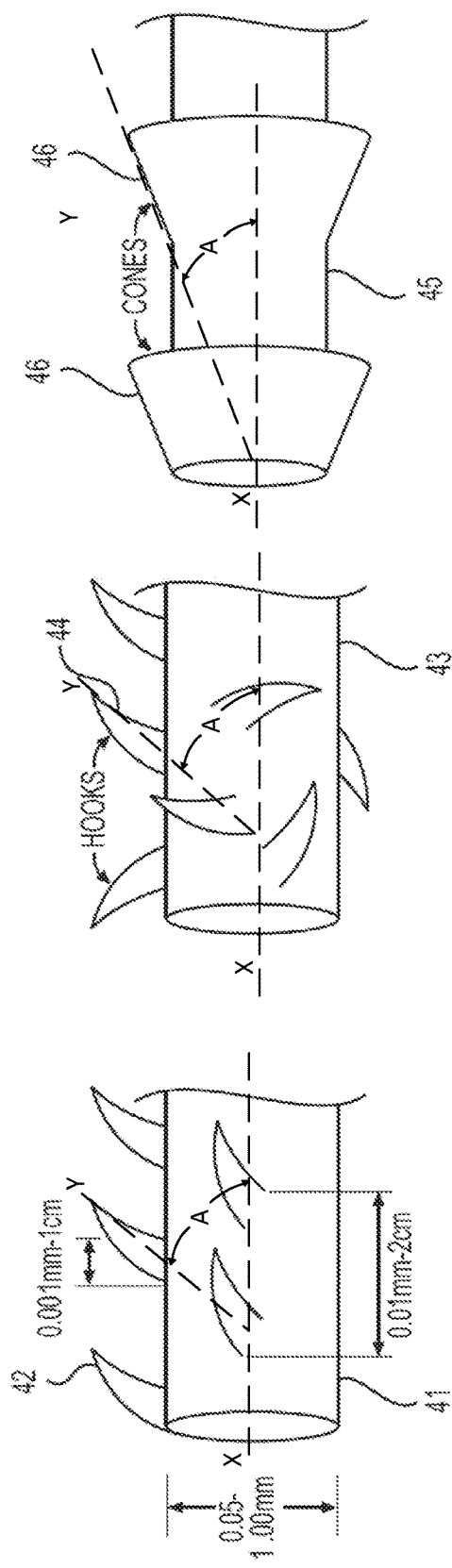

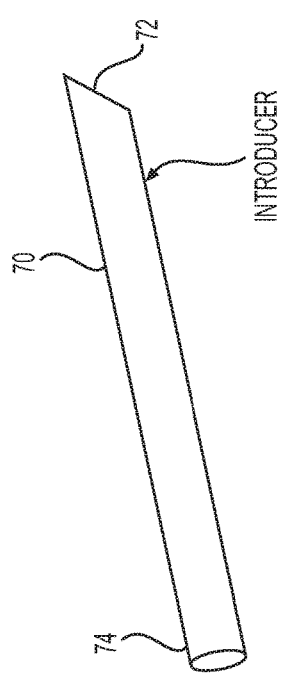
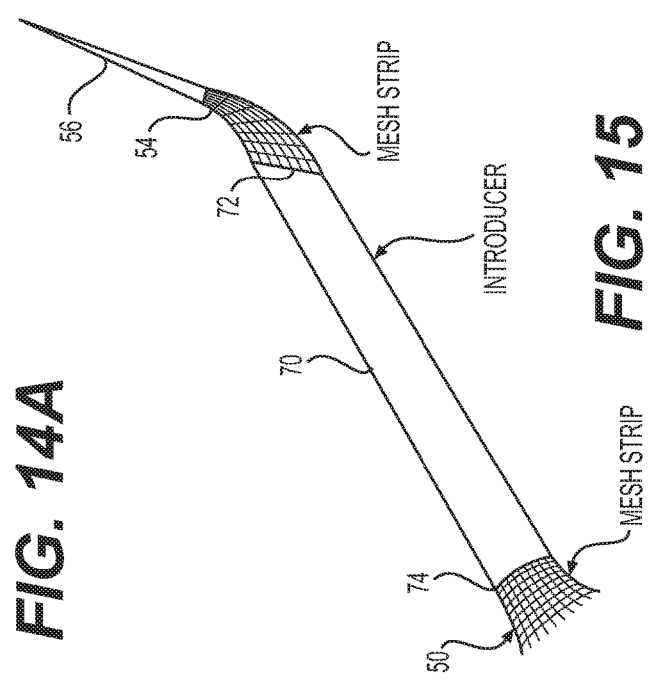

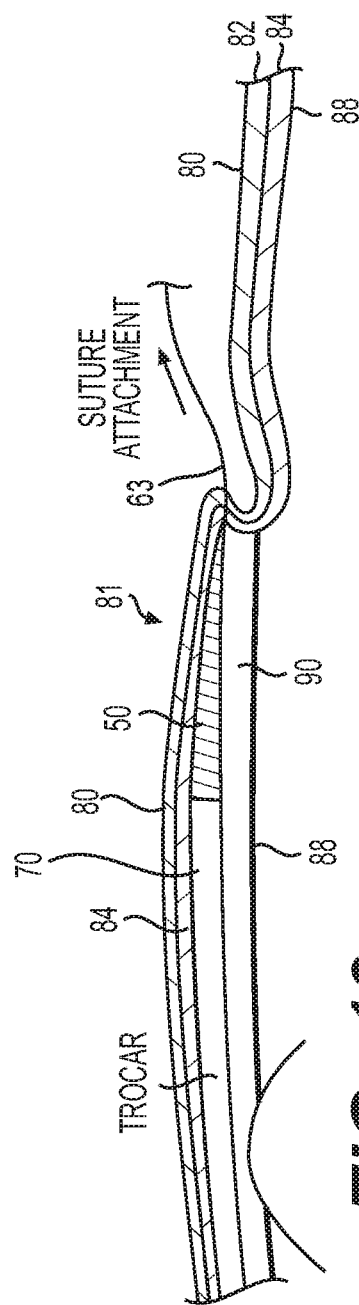
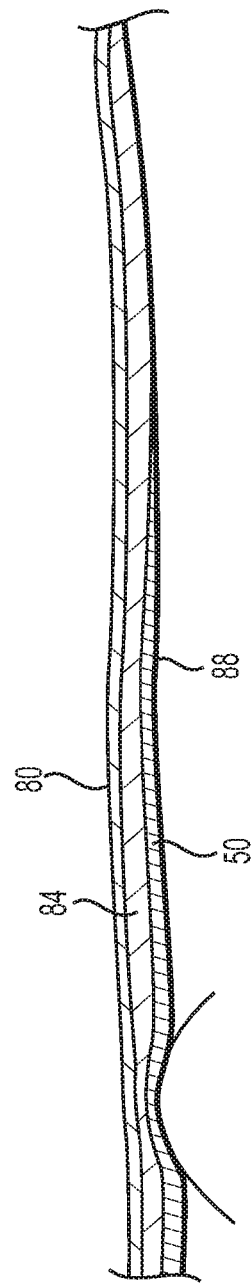

APPARATUS AND METHOD FOR LIFTING OR RESTRAINING A BODY PART

CROSS-REFERENCE TO RELATED APPLICATIONS

The present application claims the priority benefit of U.S. Provisional Patent Application 62/397,297, filed on Sep. 20, 2016 and incorporated herein by reference in its entirety.

TECHNICAL FIELD

The present disclosure relates generally to organ and tissue lifting devices and procedures, and more specifically to an apparatus and method for lifting or restraining a body part.

BACKGROUND

In 2015, there were more than 125,000 facelifts and more than 40,000 brow lifts in the U.S. The state of the art has trended towards minimally invasive procedures involving percutaneous or endoscopic interventions. For example, the "thread lift" is achieved by percutaneous insertion of Quill® or Silhouette® sutures with unidirectional anchors that grip tissue when the suture is pulled proximally, thereby suspending the soft tissue of the mid-face by a marionette-like mechanism.

DRAWINGS

While the appended claims set forth the features of the present techniques with particularity, these techniques may be best understood from the following detailed description taken in conjunction with the accompanying drawings of which:

FIG. 1 depicts a curvilinear mesh strip, according to an embodiment.

FIG. 2 depicts a rectangular mesh strip, according to an embodiment.

FIG. 3 depicts a cord, according to an embodiment.

FIG. 4 is a detailed view of a knit mesh strip, according to an embodiment.

FIG. 5 is a detailed view of a woven mesh strip, according to an embodiment.

FIG. 6 is a detailed view of a braided cord, according to an embodiment.

FIG. 7 is a detailed view of knitted fibers with anchors, according to an embodiment.

FIG. 8 is a detailed view of woven fibers with anchors, according to an embodiment.

FIG. 9 is a detailed view of cord filaments with anchors, according to an embodiment.

FIG. 10 is a detailed view of a fiber with barbs, according to an embodiment.

FIG. 11 is a detailed view of a fiber with hooks, according to an embodiment.

FIG. 12 is a detailed view of a fiber with cones, according to an embodiment.

FIG. 14A depicts an introducer, according to an embodiment.

FIG. 15 is a detailed view of an introducer with a mesh strip having a straight needle and an end fastened to the distal end of the mesh strip, according to an embodiment.

FIG. 19 shows a mesh (configured according to an embodiment) being held by the suture attachment while the introducer of FIG. 17 being withdrawn.

FIG. 20 shows the mesh of FIG. 19 (from which the introducer of FIG. 17 has been removed) remaining as a mesh layer, with its barbs or hooks holding the skin and subcutaneous layer.

DETAILED DESCRIPTION

Figure 13:
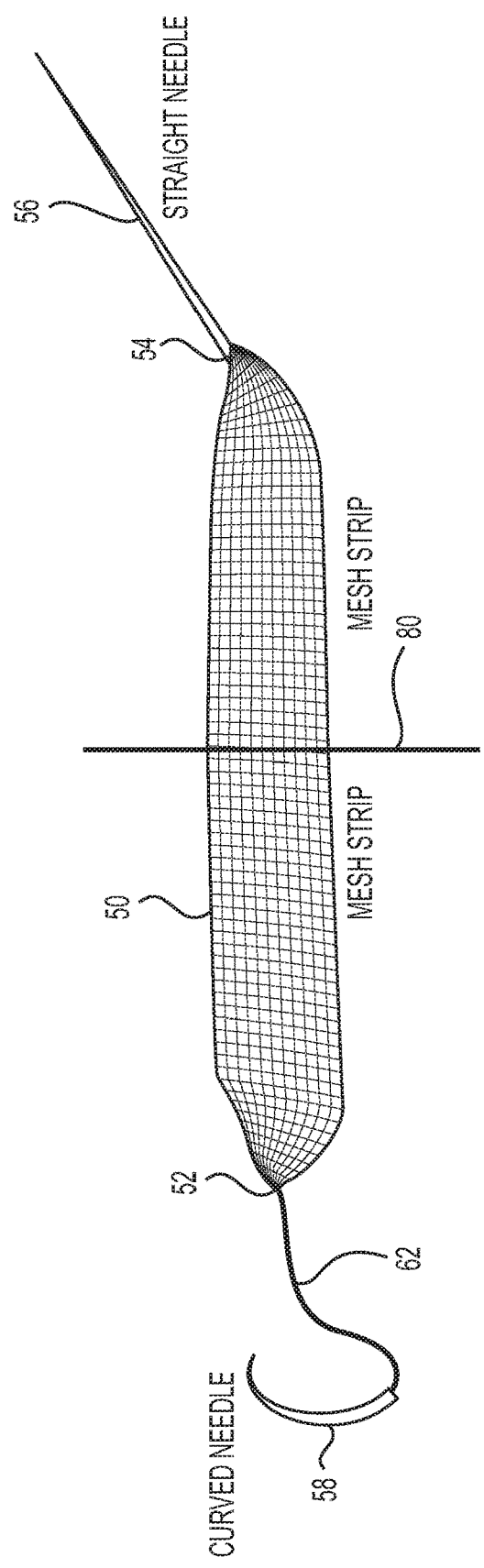
FIG. 13 is a detailed view of a mesh strip introduced through skin and subcutaneous tissue with a straight needle at a first end, according to an embodiment.

The disclosure is generally directed to assemblies and methods that include (1) strips or cords of material configured to lift, restrain, or hold whole body organs (e.g., of a human patient) or parts of body organs in desired positions via tissue anchors (e.g., barbs, hooks, or cones), (2) an introducer device that facilitates the introduction of such strips or cords into a patient, and (3) the process of inserting such strips or cords of material into a patient (e.g., using an introducer device).

As used herein, the terms "fiber" and "filament" (and their plural forms) are used interchangeably. In places where only one of these terms appears, it is to be understood that it encompasses the other term as well.

According to various embodiments, each strip or cord is made of fibers or filaments. At least some of the fibers or filaments have anchors (e.g., barbs, hooks, or cones) along their lengths at fixed or variable intervals. The fibers or filaments may be knitted or woven together (e.g., into a mesh) or braided together (e.g., into a cord). The anchors are disposed on the outer surfaces of individual fibers or filaments and are configured to engage organs (e.g., one or more layers of tissue, such as skin and underlying muscle) along the face of the strip or cord. The mesh of the strip (or the cord) and its anchors are made of an absorbable or a non-absorbable material (permanent or dissolvable within a body). The anchors are configured to engage and anchor the fibers or filaments in living tissue (e.g., tissue of a human patient).

In an embodiment, each strip or cord is inserting into tissue via an introducer. Examples of introducers include hollow guides; blunt introducers; trocars; and obturators of metal or plastic with sharpened or non-bladed tips, cannulas, and seals. In an embodiment, a distal tip of a mesh strip or cord is pulled and secured concurrently with the withdrawal of the introducer.

The assemblies described herein can be used in various procedures for elevation of muscle, subcutaneous tissue, fascia, or periosteum for facial reanimation, rejuvenation, or lifting; urogynecologic suspension; breast lifting; neck lifting; and other restraining or shaping procedures in other living tissues.

In an embodiment, a restraint or shaper, for example, a 2×9 cm strip of polydioxanone mesh with 0.5 mm hooks on one surface may be placed percutaneously, hook-side-down over the superficial muscular aponeurotic system (SMAS) through a scalp incision, and pulled proximally to suspend the subcutaneous fat of the mid-face through traction created between the hook-laden interface of the mesh and the superficial surface of the SMAS. The mesh strips and cords may be coated with collagen, cytokines or antimicrobials.

According to an embodiment, the mesh strip is spring loaded when in the introducer and is adapted for self-expanding when removed from the introducer.

In an embodiment, a system and method includes assemblies of introducers and meshes or cords and their use to achieve the objectives of distributing tension. Distributed tension leads to less "cheese wiring" across each point of tissue anchoring, and greater longevity of lift. Furthermore, distributed tension leads to less puckering or irregularity at points of tissue anchoring.

In various embodiments, barbed mesh is provided for tissue and organ lifting and for facial surgical applications. The strips of mesh, with, for example, dozens to hundreds of hooks or barbs, allow for elevation of soft tissue of the face or of other locations by traction at the interface of the mesh with the soft tissue.

Surgical applications for one or more of the embodiments described herein include breast lifting, hernia support, orthopedic anchoring, urogynecologic suspensions, neck lifting, loose tissue forming and shaping, abdominal support, rhytidectomy, rhytidoplasty (face lift), and forehead/brow lift.

In some embodiments, the anchors are configured on opposite faces of the mesh or cord for engaging all of the surrounding tissue. Example implementations of the anchors include barbs, hooks, and opposite facing hooks.

Turning to FIG. 1, a mesh strip configured according to an embodiment is shown. The mesh strip, generally labeled 12, is made up of individual fibers that have anchors and are knitted or woven together. Filaments may be used instead of fibers.

The periphery of the mesh strip 12 is curvilinear (e.g., narrower at both ends than in the middle). The curvature of the periphery of the mesh strip 12 depicted in FIG. 1 is only meant to be exemplary, and other curvatures are possible (e.g., a curvature fitting the desired locations and functions within the body of a patient). Non-curvilinear geometries for the mesh strip are also possible. For example, FIG. 2 depicts a mesh strip 14 that is rectangular, with a width that is between 0.1 and 6 centimeters and length that is between 2 and 20 centimeters. The mesh strip 14 can accommodate similar or different attachments along both ends. Other dimensions are possible for the mesh strip 14. Additionally, these (and other) dimensions may also apply to the embodiments shown in FIG. 1 and FIG. 3.

Turning to FIG. 3, a cord configured according to an embodiment is shown. The cord, generally labeled 16, is made up of individual filaments that are twisted, braided, wound, and/or bound together. Fibers may also be used instead of filaments.

Turning to FIG. 4, a magnified view of a section of mesh of the mesh strip 12 (of FIG. 1) configured according to an embodiment is shown. In this embodiment, individual fibers 22 of the mesh are knitted together.

Turning to FIG. 5, a magnified view of a section of mesh of the mesh strip 14 (of FIG. 1) configured according to an embodiment is shown. In this embodiment, individual fibers 24 of the mesh are woven together.

Turning to FIG. 6, a magnified view of an end of the cord 16 (of FIG. 1) configured according to an embodiment is shown. In this embodiment, individual filaments 29 are braided together.

Turning to FIG. 7, a magnified view of the fibers of FIG. 4 configured according to an embodiment is shown. In this embodiment, each of the individual fibers 22 has anchors 32 attached to its surface.

Turning to FIG. 8, a magnified view of the fibers of FIG. 5 configured according to an embodiment is shown. In this embodiment, each of the individual fibers or filaments 24 has barbs 34 attached to its surface.

Turning to FIG. 9, a magnified view of the filaments of FIG. 6 configured according to an embodiment is shown. In this embodiment, each of the individual filaments 24 has hooks 36 attached to its surface.

According to an embodiment, the mesh (e.g., surgical mesh) or cord described herein is created by weaving, knitting, braiding or otherwise joining together fibers or filaments (which may be made of synthetic material) with anchors.

In an embodiment, the mesh or cord described herein is created by adding anchors to pre-constructed mesh or cord.

According to an embodiment, the fibers or filaments (e.g., of any of the embodiments depicted herein) are formed with extending anchors before they are knit, woven, wound, or braided together.

In an embodiment, the mesh or cord is formed into strips at the time of weaving, knitting, or braiding. In another embodiment, the mesh or cord is cut into strips after being woven, knit, or braided.

FIG. 10 depicts a fiber or filament configured according to an embodiment. The fiber or filament, generally labelled 41, is from 0.05 to 1.00 millimeters thick and has anchors, each of which is a barb 42. Each barb 42 has a base that is from 0.001 millimeters to 2 centimeters wide. FIG. 11 depicts a fiber or filament configured according to another embodiment. The fiber or filament, generally labelled 43, has anchors, each of which is a hook 44. FIG. 12 depicts a fiber or filament configured according to still another embodiment. The fiber or filament, generally labelled 45, has anchors, each of which is a cone 46.

In each of the embodiments depicted in FIG. 10 through FIG. 12, the anchors extend from the fiber or filament along the length of the fiber or filament.

In an embodiment, each anchor extends from the fiber or filament at an angle so as to purchase tissue and pull it along the axis of the mesh strip or cord when it is pulled. For example, in the embodiments depicted in FIG. 10, FIG. 11, and FIG. 12, the axis X of the fiber or filament intersects with the axis Y of the anchor at an angle A of no more than 60 degrees.

According to an embodiment, a straight or a curved needle is attached to one or both ends of a mesh strip or a cord (e.g., to one of the mesh strips or one of the cords described herein) in any combination (e.g., a straight needle at each end, a curved needle at each end, a straight needle and one end and a curved needle at the other end). The needle (one or both) may be directly attached (e.g., cinched to the mesh strip or to the cord) or indirectly attached (e.g., attached via suture) to the mesh strip or to the cord. Furthermore, in the case of a mesh strip, there may be one or more needles attached to parts of the mesh strip other than the ends (e.g., one or more needles may be attached to the lateral edges of the strip).

In an embodiment, a sterile introducer (e.g., a trocar or a cannula) houses the strip or cord as it is introduced within the tissues of a patient. The introducers depicted in the figures are generally tubular and hollow but may, for example, be more flattened (e.g., planar) in order to accommodate a mesh strip having needles attached to the lateral edges of the mesh strip.

Turning to FIG. 13, an embodiment of a mesh strip (e.g., as previously described) having a curved needle, a suture, and a straight needle attached thereto, as well as how such an assembly is used (according to an embodiment) will now be described. The mesh strip, generally labeled 50, is introduced through skin 80 and subcutaneous tissue with a straight needle 56, which is attached to a leading distal end 54 of the mesh strip 50. Attached to the proximal end 52 of the mesh strip 50 (via a suture 62) is a curved needle 58. The curved needle 58 is used to suture (with the suture 62) the proximal end 52 of the mesh strip 50 in the skin 80 or to surrounding tissue (e.g., internal body tissue, subcutaneous tissue). The suture 62 has a first end attached to proximal end 52 of the mesh strip 50 and a second end attached to the curved needle 58. Although not depicted in FIG. 13, a cord as previously described may be used in place of the mesh strip 50.

In an embodiment, a mesh strip or cord (such as any of the mesh strips and cords described herein) is introduced into tissue via an introducer. FIGS. 14 through 20 depict an embodiment of the introducer being inserted into the tissue of a patient and a mesh strip being inserted into the patient through the use of the introducer.

Turning to FIG. 14A, an introducer configured according to an embodiment is shown. The introducer, generally labeled 70, is implemented as a trocar having a leading or distal end 72 and a trailing or proximal end 74. The distal end 72 may be sharpened for penetrating skin. During use, the proximal end 74 of the introducer 70 may be left outside the penetrated skin or may be moved within the skin. Accordingly, the mesh strip 50 is initially packed within the introducer 70. For example, the mesh strip may be folded or rolled and compressed into the introducer.

Figure 14B:
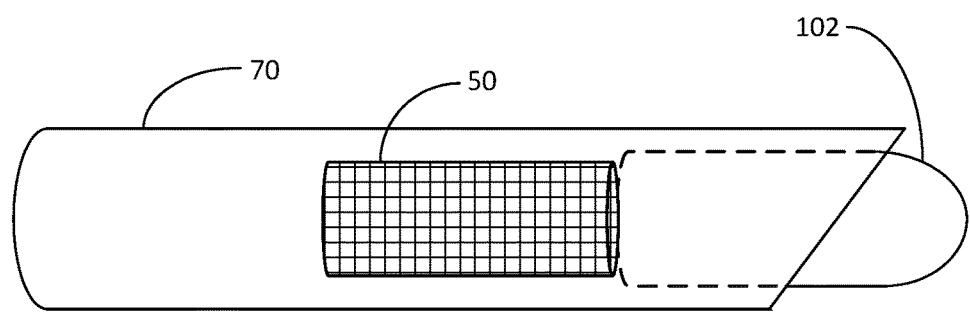
FIG. 14B depicts an introducer with a mesh strip and an obturator disposed inside the introducer, according to an embodiment.

According to an embodiment, the assembly described herein also includes a blunt obturator, as shown in FIG. 14B. The obturator 102 that is pushed out through the distal end of the introducer 70 ahead of the mesh strip 50 (or ahead of a cord, if a cord is used) so as to facilitate raising the patient's tissue in order to create a space for the subsequent implantation of the mesh strip 50. In an embodiment, the obturator 102 contains the mesh strip 50 (e.g., in an internal chamber).

According to an embodiment, a variation on the obturator implementation depicted in FIG. 14B operates as follows: The obturator is inserted into the introducer before the mesh strip (or cord). The obturator facilitates raising the patient's tissue (e.g., as it is pushed forward). The obturator is then removed. Then the mesh strip (or cord) is inserted in through the introducer (e.g., via needle and/or rod or via a secondary introducer, discussed below, or by itself).

In an embodiment, the obturator 102 opens up at its tip in order to release the mesh strip 50 (or cord if a cord is used).

Figure 14C:
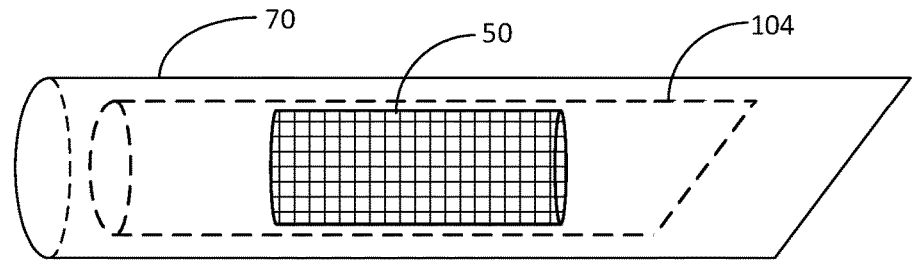
FIG. 14C depicts an introducer with a secondary introducer disposed inside the introducer and a mesh strip disposed inside the secondary introducer, according to an embodiment.

According to an embodiment, the assembly described herein also includes a secondary introducer, as shown in FIG. 14C. The secondary introducer 104, which itself is cannulated, is slideably disposed within the center bore of the primary introducer (i.e., the introducer 70) and contains the mesh strip 50 (or cord if a cord is used). Although not shown in FIG. 14C, the secondary introducer 104 includes a rod that drives a straight needle out of the distal end of the secondary introducer.

In FIG. 15, the distal end 54 of the mesh strip 50 (most of which is inside within the introducer 70) is fastened to the straight needle 56. The distal end 54 of the mesh strip 50 is shown extending out of the distal end 72 of the introducer 70.

Figure 16:
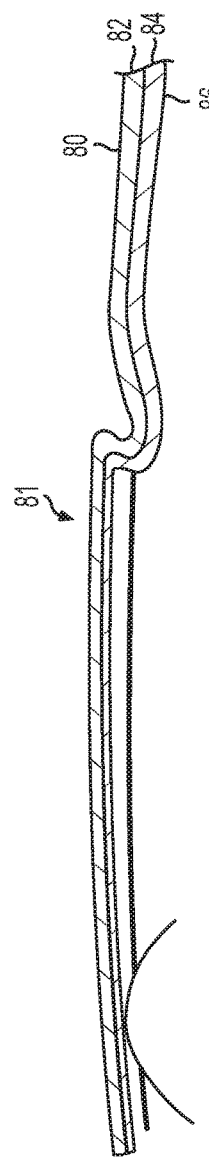
FIG. 16 shows a raised portion of skin and subcutaneous tissue under which mesh configured according to an embodiment will be introduced.
Figure 17:
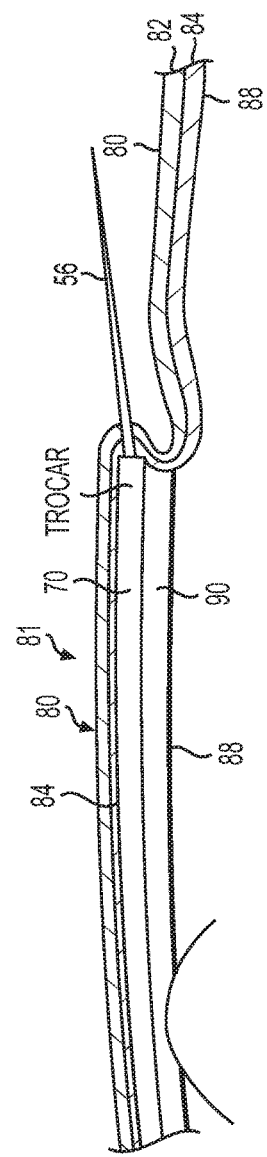
FIG. 17 shows an introducer (configured according to an embodiment—a trocar in this case) inserted in raised tissue with a straight needle projecting from the introducer.

To introduce a mesh strip or cord according to an embodiment, tissue of a patient is raised and the introducer is inserted into the space underneath the tissue. For example, FIG. 16 shows a raised portion 81 of the skin 80, subcutaneous tissue 82 and muscle tissue 84 under which the mesh will be introduced (e.g., between the muscle tissue 84 and internal body tissue 90). As shown in FIG. 17, the introducer 70 is inserted under the raised tissue with the straight needle 56 (which is shown as projecting from the introducer 70). The straight needle 56 is attached to a distal end of the mesh strip (which is, at this point, still held within the introducer 70).

According to an embodiment, the tissue may be elevated with the assistance of the introducer 70 (containing either a blunt obturator or the mesh strip 50). For example, in FIG. 16 the unlabeled space under the elevated tissue may, in fact, be occupied by the introducer 70 being used to elevate the tissue.

Figure 18:
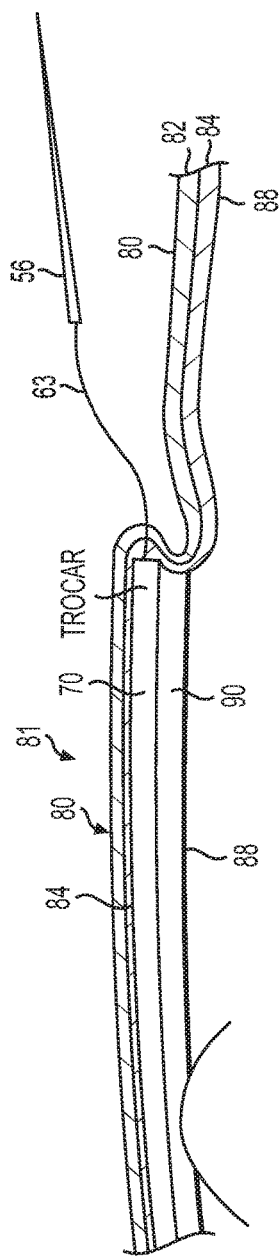
FIG. 18 shows the introducer of FIG. 17 inserted in the raised tissue with the straight needle attached to the mesh strip with a suture (which extends from the mesh strip).

Continuing the example of FIG. 16 and FIG. 17, FIG. 18 shows an introducer 70 inserted under the raised tissue (raised portion 81) with the straight needle 56. The straight needle 56 is attached to a suture 63. The suture 63 is connected to the needle 56 and to a first end of the mesh strip (or cord, if a cord is used) and is adapted to hold the first end of the mesh strip (or cord) within the body while the inserter 70 is being withdrawn for the purpose of releasing the mesh strip or cord in situ within the body. The suture 63 is used to secure the distal end of the mesh strip or cord (e.g., under the skin of the patient at the distal extent if the dissection). Put another way, the suture 63 is meant to hold tension while removing the introducer 70, but it is actually the anchors that hold the mesh strip 50 in place distally, such that the suture 63 may be cut or otherwise removed distally after the introducer has been remove proximally.

Turning to FIG. 19, after the distal end of the mesh strip 50 is secured (with the suture 63), the introducer 70 is withdrawn. As the introducer 70 is withdrawn, the mesh strip 50 remains in place. FIG. 20 shows how, after the introducer 70 has been withdrawn, the mesh strip 50 forms a mesh layer. The mesh strip 50 and its anchors (barbs, hooks, or cones) holds the skin and subcutaneous layer, which can be pulled cranially, for example.

A method carried out according to an embodiment will now be described with reference to FIG. 1 through FIG. 20. The method includes one or more of the following actions: (a) providing an introducer (e.g., introducer trocar 70), providing a mesh (e.g., mesh strip 50) in the introducer, (b) providing anchoring protrusions (e.g., barbs, hooks, or cones as shown in FIG. 7 through FIG. 12) on the mesh, introducing the introducer between tissues in a body (e.g., between the muscle tissue 84 and internal body tissue 90), holding a first end of the mesh (the proximal end 52) within the body (e.g., using the curved needle 58), withdrawing the introducer from the body while holding the first end of the mesh within the body, and fastening a second end of the mesh (e.g., the leading distal end 54) within the body after the introducer is fully withdrawn from the body.

The method includes automatically expanding the mesh within the body, engaging tissue on at least one side of the mesh with the anchoring protrusions (e.g., barbs, hooks, or cones) on the mesh and moving the tissue on the at least one side of the mesh (e.g., as in the elevated portion 81) by moving the mesh before fastening the first end of the mesh within the body.

In an embodiment, the actions of elevating and securing the first end in the body and concurrently elevating the mesh and elevating surrounding tissue with the mesh holds the tissues in desired new positions and restraints, and lifts organs and other parts of a body for promoting tissue growth through and around the mesh or cords.

In the embodiments described herein, the mesh strips or cords may be used for facelifts. In other parts of the body, the mesh strips or cords may be used to hold or urge any tissue or organ to a different desired position or to restrain tissues or organs from moving to undesired positions.

In the embodiments described herein, the mesh strip may be laterally folded or otherwise compressed into the introducer and when released may return to its normal outspread condition. Surgical instruments may be used to spread or to assist spreading of the mesh strips laterally to desired positions.

As shown in the examples of FIG. 16 through FIG. 20, space may be provided and retained for lateral expansion of the mesh strip into its desired position before releasing the outward tissue to close the space.

In an embodiment, the mesh of the mesh strip includes a plurality of synthetic fibers or filaments formed into a curvilinear strip, rectangular strip or cord. The mesh has small hooks, cones or barb anchors at fixed or variable intervals along some or all of the fibers or filaments. The mesh and its anchors are made of an absorbable or a non-absorbable material.

According to an embodiment, a method of introducing one or more strips or cords (as previously described) into living tissue involves housing each strip or cord within a sterile introducer (e.g., a trocar or cannula) and introducing each strip or cord into the tissue (e.g., subcutaneously) via an introducer. An introducer may be, for example, a hollow guide, a blunt piece, a trocar, or an obturator. The introducer may be made, for example, of metal or plastic and may have one or more of a tip (sharpened or non-bladed), a cannula, and seal.

In an embodiment, a method of introducing one or more strips or cords involves pulling and securing the distal tips of the mesh and, concurrently, withdrawing the one or more introducers.

According to an embodiment, barbed mesh is provided for tissue and organ lifting and for facial surgical applications. The strips of mesh, with, for example, dozens to hundreds of hooks or barbs, allow for elevation of soft tissue of a patient's face or of other locations on the patient by traction at the interface of the mesh with the soft tissue.

An embodiment of the disclosure includes structures that lift or restrain whole body organs or parts of body organs. Such structures include an introducer, mesh or cord held with an introducer configured to introduce a mesh or cord into and between body parts. The mesh or cord is configured to hold body parts in desired positions. Outer surface anchors on the mesh or cord is configured to engage body parts along a face of the mesh or cord.

It should be understood that the embodiments described herein should be considered in a descriptive sense only and not for purposes of limitation. Descriptions of features or aspects within each embodiment should typically be considered as available for other similar features or aspects in other embodiments. It will be understood by those of ordinary skill in the art that various changes in form and details may be made therein without departing from their spirit and scope.

What is claimed is:

1. A method for lifting one or more layers of tissue in a body, the method comprising:
   introducing an introducer under the one or more layers, wherein the introducer holds a mesh strip therein,
   wherein the mesh strip comprises a plurality of fibers woven or braided together in a tubular configuration that is hollow along a longitudinal axis, the plurality of fibers comprising a plurality of anchors extending therefrom and configured to anchor onto tissue of a body part in the body;
   expanding the mesh strip within the body in order to lift or restrain the body part;
   engaging a layer of the one or more layers of tissue on at least one side of the mesh strip with at least some of the plurality of anchors on the mesh strip;
   holding a first end of the mesh strip within the body;
   withdrawing the introducer from the body while holding the first end of the mesh strip within the body;
   moving the engaged layer on the at least one side of the mesh strip; and
   fastening a second end of the mesh strip within the body after the introducer is withdrawn from the body.

2. The method of claim 1, further comprising:
   concurrently elevating the mesh strip and elevating surrounding tissue with the mesh strip.

3. The method of claim 1, wherein holding the first end of the mesh strip within the body comprises securing the first end with a suture, the method further comprising cutting the suture after withdrawing the introducer.

4. The method of claim 1, wherein the first end of the mesh strip is held within the body by the at least some of the anchors.

5. The method of claim 1, wherein the body part is a patient's breast.

6. The method of claim 1, wherein the body part is a patient's face.

7. The method of claim 1, wherein the body part is a patient's neck.

\* \* \* \* \*